United States Patent [19]

Coughlin

[11] 4,444,778
[45] Apr. 24, 1984

[54] METHOD AND COMPOSITION FOR TREATING ATHEROSCLEROSIS

[76] Inventor: Shaun R. Coughlin, 130 Bowdoin St., Apt. 1006, Boston, Mass. 02108

[21] Appl. No.: 407,960

[22] Filed: Aug. 13, 1982

Related U.S. Application Data

[63] Continuation-in-part of Ser. No. 297,076, Aug. 27, 1981, abandoned.

[51] Int. Cl.³ .............................................. A61K 31/475
[52] U.S. Cl. ...................................... 424/262; 424/250; 424/251; 424/261; 424/267; 424/304; 424/319; 424/330
[58] Field of Search ............... 424/262, 267, 250, 251, 424/261, 330, 319, 304

[56] References Cited

U.S. PATENT DOCUMENTS

| | | | |
|---|---|---|---|
| 3,846,476 | 11/1974 | Kaiser et al. | 424/300 X |
| 3,852,338 | 12/1974 | Kaiser et al. | 424/319 X |
| 4,224,343 | 9/1980 | Wurtman | 424/319 |

OTHER PUBLICATIONS

Yamori, Y., et al., *J. Pharm. Pharmac.*, 1972, 24 (9), 690–695.
Goodman and Gilman's *The Pharmacological Basis of Therapeutics,* 6th Ed., Macmillan, New York, 1980, pp. 202–203.
Ross, R., et al., *New England J. Med.*, 295, 369–377 and 420–425 (1976).
Friedman, R., et al., *Prog. Hemostasis and Thromb.*, 4, 249–278 (1978).
Coughlin, S., et al., *Nature,* 288, 600–602 (1980).
Goldberg, I., et al., *Science,* 205, 920–922 (1979).
Shimamoto, T., *Acta Path. Jap.* 19 (1), 15–43 (1969).

*Primary Examiner*—Richard A. Schwartz
*Attorney, Agent, or Firm*—Richard P. Crowley

[57] ABSTRACT

A method of improving the arteriosclerotic condition in an animal having arteriosclerosis or having a high risk of developing arteriosclerosis, which method comprises administering an effective amount of a serotonin regulating agent, to inhibit the biological activity of serotonin within the blood vessels, thereby inhibiting the proliferation of smooth muscle cells, which has been found to cause or contribute to an arteriosclerotic condition.

31 Claims, No Drawings

METHOD AND COMPOSITION FOR TREATING ATHEROSCLEROSIS

This application is a continuation-in-part of U.S. patent application Ser. No. 297,076, filed Aug. 27, 1981, now abandoned.

BACKGROUND OF THE INVENTION

The most widely accepted model (Ross, et al, New England Journal of Medicine, 295, 369-377 and 420-425, 1976; and Friedman, et al, Prog. Hemostasis and Thrombosis, 4, 249-278, 1978) for the process of atherogenesis involves hemodynamic, immunologic or metabolic injury to the endothelial lining of a blood vessel, which causes the underlying smooth muscle layer to be exposed to blood elements. In this model, circulating platelets adhere to the damaged blood vessel wall, releasing their granule contents. This event appears to be vital in initiating the next step in the atherogenic process, which is the migration of smooth muscle cells from the medial layer of the blood vessel, where they normally reside, into the arterial intima (the inner layer of the vessel) and their subsequent proliferation. These intimal smooth muscle cells synthesize extracellular matrix material and imbibe lipid to produce the foam cells seen in atherosclerotic blood vessels. It is this overgrowth of smooth muscle cells, together with increased matrix material and lipid, which narrows the blood vessel lumen, compromising blood flow and causing an increased tendency for blood to clot and obstruct the affected vessel. Strategies for the prophylaxis and treatment of atherogenesis in the past have been directed at reducing risk factors for the disease, such as lowering blood pressure in hypertensive subjects, treating diabetics and reducing elevated cholesterol levels in hypercholesterolemic subjects.

SUMMARY OF THE INVENTION

Since local accumulation of smooth muscle cells with the arterial intima is central to the development of atherosclerotic lesions, one very important strategy for the prophylaxis and treatment of arteriosclerosis is to suppress smooth muscle cell proliferation. Blood platelets are the likely bearers of the messenger for smooth muscle proliferation. After the endothelial lining of the blood vessel has been damaged, platelets carpet the denuded area, liberating their granule contents into the circulation and into the vessel wall. Serotonin, calcium, adenosine triphosphate and adenosine diphosphate are liberated from platelet dense bodies. Platelet alpha granules release beta-thromboglobulin, platelet factor IV, platelet fibrinogen and platelet-derived growth factor. The functions of these various compounds are not well understood, although it appears that they are important to hemostasis and/or repair of the damaged vessel. Platelet-derived growth factor has been shown by others to be a mitogen for smooth muscle cells. Due to the nature of platelet-derived growth factor, it has not been possible to access the role played by this molecule in stimulation of smooth muscle proliferation in vivo. Prior to the present invention, a role for platelet serotonin, in stimulating smooth muscle cell proliferation, had also not been known or demonstrated. It has now been found that serotonin is a potent promoter of smooth muscle proliferation in cell culture and is important in mediating smooth muscle cell proliferation after vascular injury in vivo. It is the object of this invention to control this biological signal for smooth muscle proliferation in the blood vessel intima so as to control the condition of arteriosclerosis. It is especially applicable where hypertension, existing arteriosclerosis, vascular surgery associated with accelerated smooth muscle proliferation and risk of vessel occlusion, or diabetes significantly increase the risk of arteriosclerosis development.

Accordingly, the present invention comprises the use of agents either alone or in combination to inhibit the smooth muscle cell proliferation activity of serotonin within blood vessels; to limit and reverse the progression of arteriosclerosis resulting from smooth muscle cell proliferation; and to prevent the development of the disease where there is a high risk of developing this condition. In particular, this invention provides a method and pharmaceutical compositions useful in the treatment of arteriosclerosis and in limiting the progression of arteriosclerosis resulting from vascular smooth muscle cell proliferation. More particularly, this invention provides a method of inhibiting smooth muscle cell proliferation in the injured blood vessel of a mammal and pharmaceutical compositions for use in the method, which comprises administering to the mammal a serotonin regulating agent in an effective smooth muscle proliferation inhibiting amount. The term "agent" as used here and in the claims, means both a single agent or a combination of agents.

DESCRIPTION OF THE EMBODIMENTS

In order to interfere with the signal for smooth muscle cell proliferation, various methods and agents can be employed to reduce the biological activity of platelet-released serotonin within the blood vessels. The methods used to reduce serotonin in the blood vessels may include, alone or in combination, the use of a diet lean or poor in tryptophan, which decreases the amount of serotonin precursor available for conversion to serotonin, or the administration orally, parenterally or otherwise of an agent or agents which interferes with, blocks, inhibits or decreases any serotonin precursor or serotonin itself in the blood. The diet and/or anti-serotonin agent or agents may be used in combination with other known drugs or treatments for arteriosclerotic conditions. In general, the relevant serotonin antagonist categories, whether used alone or in combination with antiplatelet drugs, antihypertensive agents, lipid-lowering techniques or other medical treatments or drugs, include, but are not limited to: serotonin receptor blockers; serotonin storage blockers; serotonin uptake blockers; and agents or diets which inhibit the synthesis of serotonin or the availabiity of its precursor tryptophan.

The activity of serotonin in the blood may be reduced by an artificial diet, as indicated above, markedly low or lacking in the essential amino acid tryptophan, which is needed for the synthesis of serotonin. This is accomplished through the use of a corn-based diet, which is tryptophan-poor, or an artificial amino-acid mixture from which tryptophan is deleted. Because of undesirable side effects resulting from the absence of an essential amino acid, the use of anti-serotonin agents is preferred in the present invention.

A first group of agents which may be used to inhibit smooth muscle cell proliferation are those which interfere with the conversion of tryptophan to serotonin, specifically tryptophan hydroxylase inhibitors (for example, p-chloro-phenylalanine) and aromatic amino acid decarboxylase inhibitors (for example, carbidopa).

Serotonin is synthesized in the gut enterochromaffin cells and in the central nervous sytem and is taken up by the blood platelet via a specific uptake system and stored in platelet organelles known as dense bodies. The first and most specific enzyme in this pathway is tryptophan hydroxylase. This enzyme is the rate-limiting compound in serotonin synthesis, and blocking the activity of this enzyme will decrease the amount of serotonin produced. Tryptophan hydroxylase inhibitors, such as p-chloro-phenylalanine, thus reduce the quantity of serotonin available for action at the blood vessel wall and are useful for the treatment of atherosclerosis. The second enzyme involved in the synthesis of serotonin is 5-hydroxytryptophan decarboxylase. Agents that selectively block the activity of this enzyme also decrease serotonin production and, thus, are useful in the treatment of atherosclerosis. Carbidopa is an example of a prototype drug of this type as indicated above.

A second group of anti-serotonin agents which may be used are serotonin uptake blockers, for example, fluoxetine or amitriptyline, which prevent serotonin uptake by platelets. Platelet serotonin after synthesis in the gut enterochromaffin cells, is released into the blood, where it is rapidly transported into the blood platelet via a specific transport system, or degraded by the ubiquitous enzyme, monoamine oxidase. Inhibition of the platelet's serotonin transport system therefore leads to functional depletion of platelet serotonin stores; and hence, less serotonin is available to act at the blood vessel wall. Existing serotonin uptake blockers, such as amitriptyline (Elavil) or fluoxetine, are therefore useful agents in the prophylaxis and treatment of arteriosclerosis.

Agents that interfere with serotonin storage may also be employed to deplete platelet serotonin stores in the dense bodies. Tetrabenazine and drugs of the Rauwolfia alkaloid class, such as reserpine (serpasil, Raurine, Reserpoid, etc.), interfere with serotonin storage, effectively depleting the platelet of its serotonin content. It has been found that reserpine, in combination with the serotonin receptor blocker methiothepin, can reduce markedly smooth muscle proliferation after experimental vascular injury.

Serotonin receptor blockers, such as methiothepin, metergoline, methysergide, cyproheptadine and especially pizotyline (4-[1-methyl-4-piperidylidene]-9,10-dihydro-4H-benzo[4,5]cyclohepta[1,2-b]thiophene) are the preferred group employed to interfere specifically with and inhibits the proliferating action of serotonin on smooth muscle cells. Serotonin receptor blockers provide the most effective and specific approach to limiting the ability of platelet-released serotonin to stimulate smooth muscle cell proliferation. Released serotonin acts at specific receptors on the smooth muscle cell surface and this interaction can be blocked by serotonin antagonists, such as those mentioned above and also butyrophenones such as spiroperidol and haloperidol; and others such as cinanserin and mianserin. Pizotyline and methiothepin have been found to be remarkably effective in preventing smooth muscle cell proliferation after experimental vascular injury.

In addition to the serotonin antagonist categories above, agents which act as inhibitors or platelet activation will decrease platelet aggregation and platelet adhesion to injured blood vessel walls, thereby also decreasing serotonin release. Examples of agents that act in this fashion are: (1) agents that act to raise platelet cyclic AMP, either by increasing its synthesis, for example, prostacyclin or prostaglandin $E_1$ and their analogues or by decreasing its degradation, for example, the phosphodiesterase inhibitors, sulfinpyrazone or dipyridamole; (2) agents that decrease platelet thromboxane $A_2$ synthesis, for example, cyclooxygenase inhibitors, such as aspirin or indomethacin, or thromboxane synthetase inhibitors, such as imidazoles; and (3) agents that block calcium influx into platelets, that is, calcium channel blockers, such as verapamil. The use of agents in this group, for the purpose of inhibiting platelet/vessel wall interaction and thereby decreasing smooth muscle proliferation, are already known in the art. However, these agents are useful in combination with compounds specifically directed at blocking the action of serotonin, for example, pizotyline and methiothepin.

Each of the above antiserotonin strategies may be employed either alone or in combination with another antiserotonin intervention approach disclosed or in combination with antiplatelet drugs or other appropriate medical therapies, such as antihypertensive agents, lipid-lowering techniques, etc. In one aspect of this invention, novel pharmaceutical compositions are provided comprising at least two serotonin antagonists from a different group set out above. By administering a combination of agents, each of which acts with relative specificity at a different site in the pathway from tryptophan intake to serotonin's action at the smooth muscle receptor, the possibility of achieving maximum inhibition of serotonin's action is increased. In addition, the relative specificity of the intervention is increased, and the dosages of the individual agents can be minimized to avoid undesirable side effects, which are well known in the art. The preferred strategy is the use of a serotonin receptor blocker alone or in combination with one or more antiserotonin agents selected from serotonin synthesis inhibitors, serotonin storage blockers, serotonin uptake blockers or blood platelet inhibitors, especially serotonin storage blockers and inhibitors of platelet function.

While the specific pharmaceutical agents set forth above are known in the art, they have not been utilized for the prophylaxis or treatment of arteriosclerosis by inhibiting smooth muscle cell proliferation; and they have not been utilized in combinations for such treatment. Other serotonin receptor blockers, which may be used in this invention include ketanserin, desipramine, imipramine, chlorimipramine, protriptylene, dibenzepine, amitryptyline, doxepin, prothiadene, pirandamine, spirobenzofuran, ciclazindol, nefopam, deximafen, daledalin, amedalin, quipazine, trazodone, zimelidine, tofenacine, fenetazole and fenflurame. Additional compounds which have serotonin antagonist activity and can be used are 11-amino-1,5-methano-1,2,5,6-tetrahydrobenzocine; 1-methylamino-4-phenyl-1,2,3,4-tetrahydronaphthylene; 6-cyano-1,3-dihydro-3-dimethylaminopropyl-3-(p-fluorophenyl)-isobenzofuran; 4-benzyl-1-(2-benzofurancarbonyl)-piperidide, 1,4-ethano-4-phenyl-cyclohexylamine, α-(p-chlorophenyl)-2-methylaminomethylbenzyl alcohol; α-(2-methylaminoethyl)-2-methoxy or 4-trifluoromethylphenylbenzyl ether or p-anisyl-(1-methyl-4-phenyl-3-pipecolinyl)-ether.

Inhibitors of serotonin synthesis, uptake or storage would preferably be administered orally in doses sufficient to cause a fall in platelet serotonin levels. The actual and effective dose of drug used for these purposes is determined by monitoring platelet serotonin content essentially as described by Rao, et al (An Improved Method for the Extraction of Endogenous Platelet Serotonin, J. Lab. Clin. Med., 87, No. 1, 129–137, 1976). Inhibitors of platelet function have been used in humans; and the actual dose of inhibitor to be employed may be determined by monitoring inhibition of ex vivo platelet aggregation essentially as described by R. Friedman and E. Burns ("Role of Platelets in the proliferative response of the Injured Artery"; Prog. Hemostasis and Thrombosis; 4, 249–278, 1978). Serotonin receptor blockers have also been used in humans, and the actual dose of the blocker to be used can also be determined by monitoring of ex vivo platelet aggregation in response to serotonin and determining the amount of serotonin receptor blocker necessary to block this effect. Additional methods for monitoring serotonin, serotonin uptake or serotonin uptake inhibition in blood platelet are described by Wielosz, et al (Naunyn-Schniedeberg's Arch. Pharmacol. 296, 59–65, 1976); O. Lingjaerde (Adv. Biosci, 31, 161–167, 1981); Tuomisto (J. Pharm. Pharmac., 26, 92–100; 1974); Richter, et al (J. Pharm. Pharmac., 26, 763–770, 1974); and Tuomisto, et al (Clin. Pharmacol. Ther., 63, No. 11, 1714–1718, 1974).

In order to demonstrate the efficacy of serotonin antagonists as inhibitors of smooth muscle proliferation after vascular injury (and thus as effective agents in ameliorating the development of atheromas), the following experimental strategy, among others, has been employed. The use of serotonin antagonists in preventing or impeding arteriosclerotic lesion is indicated in vivo essentially in accordance with the de-endothelialization procedure of Tiell, et al (Influence of the Pituitary on Arterial Intima Proliferation in the Rat, Circulation Research, Vol. 42, No. 5, 644–149, May 1978). Male Sprague-Dawley rats weighing 300–360 grams are fed a constant formula rodent lab chow and water ad libitum for two weeks prior to the start of the test. For two days before de-endothelialization and for the following 14 days until sacrifice, the animals receive either a placebo or 1 to 200 milligrams per kilogram per day of test compound. On the day of de-endothelialization, the drug is administered intravenously at one-tenth the oral dosage. De-endothelialization is carried out in the aortas of the anesthetized animals by balloon catheterization. The animals are weighed daily from the time of dosing and their behavior is recorded 3 to 4 hours following administration of the test compound. Fourteen days after catheterization, whole body perfusion fixation is carried out at 37° C. with 3% buffered glutaraldehyde in 0.15 M sodium cacodylate at pH 7.4 under 90–100 millimeters hydrostatic pressure. The aorta is removed, cut into 10 equal segments, and following two additional hours in the buffered glutaraldehyde, is treated with 1% osmium tetroxide, dehydrated, infiltrated with Squer's resin and cured. The segments are stained with Stevenal's blue and basic fuchsin, and the lesion areas is determined with a zeiss standard microscope and Videoplan computerized image analyzer. Please see examples for results.

For the treatment and prophylaxis of atherosclerosis, the inhibitors of serotonin synthesis, the serotonin uptake, storage, and receptor blockers and the anti-platelet agents may be administered orally or parenterally as such or admixed with conventional pharmaceutical carriers. They may be administered orally in such forms as tablets, dispersible powders, ranules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The effective amount of serotonin antagonist employed in the treatment of arteriosclerosis vary widely depending on the particular compound employed, the mode of administration and the severity of the condition being treated. The optimum dose is readily determined by the methods indicated above. The dose should be sufficient to reduce smooth muscle cell proliferation by at least 20% and preferably from 40% to 95%. In general satisfactory results in the treatment of artherosclerosis are obtained when a serotonin receptor blocker is administered at a daily dosage of from about 2 milligram to about 200 milligrams, preferably 15 to 50 milligrams per kilogram of animal body weight, preferably given orally once a day, or in sustained release form. For most large mammals, the total daily dosage is from about 1 milligram to about 1000 milligrams, preferably 5 to 200 milligrams. Unit dosage forms suitable for internal use comprise from about 1 milligram to about 500 milligrams, in intimate admixture with a solid or liquid, pharmaceutically acceptable carrier.

The following examples illustrate the present invention and are not intended to limit the invention.

EXAMPLE 1

Smooth muscle cells are grown from explants of bovine aortic media as described by Coughlin, et al (Platelet-Dependent Stimulation of Prostacyclin Synthesis by Platelet Derived Growth Factor, Nature, 288, pp. 600–602, 1980). Cells are seeded at $10^5$ cells per 35 mm tissue culture well in Dulbecco's Modified Eagle Medium containing 10% calf serum and allowed to grow for 24 hours. The serum-containing medium is then removed and the cells are allowed to become quiescent in Medium 199 for 24 hours. The quiescent cultures are then incubated for 72 hours in Medium 199, with or without the mitogen to be tested. After the 72-hour incubation period, the cells are harvested for cell-number determination by Coulter Counter.

Table I shows that more smooth muscle cells are present in cultures that are treated with $10^5$ moles of serotonin. This effect is observed in both the presence and absence of 2% human platelet-poor plasma which has been reported to allow for better expression of mitogenic activity. Platelet-derived growth factor (PDGF), a known mitogen for smooth muscle cells, is also seen to be active in this system.

TABLE I

| Treatment | Cell Number/Plate ($\times 10^{-5}$) | |
|---|---|---|
| | No Plasma | Plasma |
| Control | 6.60 ± 0.20 | 5.75 ± 0.14 |
| Serotonin ($10^{-5}$M) | 8.34 ± 0.43 | 12.19 ± 0.13 |
| PDGF (8 ng/ml) | 9.65 ± 0.29 | 14.24 ± 0.04 |
| Serotonin + PDGF (8 ng/ml) | 10.51 ± 0.27 | 14.36 ± 0.14 |

Mean ± SEM (n = 6)

EXAMPLE 2

Smooth muscle cells are seeded and made quiescent as described in Example 1. Cultures are then treated with serotonin, PDGF or cyproheptadine, a serotonin receptor blocker. The cultures are then incubated for 96 hours in Medium 199 containing 2.5% platelet-poor plasma and the treatment to be tested. The results are set forth in Table II.

This example shows that serotonin increases the number of smooth muscle cells present at the end of the test period, and that this increase is attenuated by the serotonin receptor blocker, cyproheptadine. Serotonin causes increases in smooth muscle cell number above and beyond those caused by low concentrations of PDGF, and these serotonin-induced increases are again attenuated by cyproheptadine. Fetal calf serum, which is known to promote smooth muscle proliferation maximally is employed as a positive control. Similar results are obtained using the serotonin receptor blockers, metergoline and methiothepin. Other serotonin receptor blockers, such as pizotyline, methysergide, spiroperidol mianserin, yield similar results.

TABLE II

| Treatment | Cell Number/Plate ($\times 10^{-5}$) | % Maximum* |
|---|---|---|
| Control | 5.0 ± 0.19 | 0 |
| Serotonin $10^{-5}$M | 7.68 ± 0.12 | 33 |
| Serotonin + Cyproheptadine $10^{-6}$M | 5.87 ± 0.15 | 10 |
| PDGF 0.5 ng/ml | 8.11 ± 0.23 | 39 |
| PDGF 0.5 ng/ml + Serotonin | 10.40 ± 0.06 | 68 |
| PDGF 0.5 ng/ml + Serotonin + Cyproheptadine | 9.57 ± 0.14 | 58 |
| PDGF 4.0 ng/ml | 10.66 ± 0.16 | 72 |
| PDGF 4.0 ng/ml + Serotonin | 12.01 ± 0.09 | 89 |
| PDGF 4.0 ng/ml + Serotonin + Cyproheptadine | 11.11 ± 0.07 | 77 |
| 1% Fetal Calf Serum | 8.24 ± 0.20 | 40 |
| 5% Fetal Calf Serum | 11.16 ± 0.11 | 78 |
| 10% Fetal Calf Serum | 12.86 ± 0.11 | 100 |

BASMC P₃ Mean ± SEM (n = 6) 2.5% 96-hour incubation
* % Maximum = (Value for Treatment group − value for Control group) ÷ (Value for 10% Fetal Calf Serum − value for Control group) × 100

EXAMPLE 3

In this experiment, stimulation of $^3$H-thymidine incorporation is used as an index of the ability of a compound to promote smooth muscle cell proliferation. Smooth muscle cells are seeded in 96 well Linbro racks (5 mm diameter/well) and allowed to grow for 72 hours. Cells are next allowed to become quiescent in Medium 199 for 24 hours. To start an incubation, cells are incubated with 200 ul of Medium 199 containing 2.5% platelet-poor plasma, $^3$H-thymidine (5uCI/ml) and treatment or control. After approximately 36 hours, the cells are washed with saline, fixed with 10% TCA, washed with water, lysed with 1% SDS, and the lysate counted for $^3$H. This procedure allows the investigator to assess the amount of $^3$H-thymidine taken up by smooth muscle cells and incorporated into DNA. This process occurs to the extent that cells are proliferating and, hence, is used to test the ability of substances to stimulate cell proliferation.

The data of Table III obtained in this test shows that serotonin stimulates smooth muscle cell proliferation, as indicated by increased $^3$H-thymidine incorporation, in a dose-dependent manner. Furthermore, the results show that the serotonin receptor blocker, cyproheptadine (cypro, $10^{-7}$ M) attenuates this response to serotonin. Platelet-derived growth factor (1 ng/ml) known to stimulate smooth muscle cell proliferation, also is shown to increase thymidine incorporation.

TABLE III

| Treatment | CPM/Well ($\times 10^{-3}$) | % Increase |
|---|---|---|
| Control | 90.0 ± 7.2 | 0 |
| 1% FCS | 290.3 ± 25.9 | 222 |
| Serotonin $10^{-7}$M | 139.8 ± 11.9 | 55 |
| Serotonin $10^{-6}$M | 306.4 ± 3.1 | 240 |
| Serotonin $10^{-7}$M + Cypro | 85.9 ± 6.5 | −4 |
| Serotonin $10^{-6}$M + Cypro | 237.4 ± 23.8 | 163 |
| Platelet-derived growth factor | 454.7 ± 28.3 | 405 |

Mean ± SEM (n = 4)
FCS = Fetal Calf Serum

Similar results are obtained when the cyproheptadine is replaced by other serotonin receptor blockers such as pizotyline.

EXAMPLE 4

This example demonstrates that interventions which reduce the activity of serotonin within blood vessels in the whole animal dramatically reduce the proliferation of smooth muscle cells after vascular injury. Rat aortas are denuded of endothelium by passing a catheter with an inflated balloon at its tip down the length of the blood vessel. In animal models, this type of vascular injury has been shown by Goldberg, et al (Vascular Smooth Muscle Cell Kinetics: A New Assay For Studying Patterns of Cellular Proliferation In Vivo, Science, 205, 920–922, 1979), to stimulate formation of vascular lesions resembling those of human atherosclerosis 48 hours after injury. The rats are injected intravenously with $^3$H-thymidine, which is incorporated into the DNA of proliferating smooth muscle cells. After one hour, the specific activity of aortic smooth muscle cell DNA is determined and used as an index of smooth muscle cell proliferation in the injured vessel wall. The data obtained are set forth in Table IV.

Pretreatment of animals with the serotonin receptor blocker, methiothepin (10 mg/kg i.p., b.i.d.) leads to a marked inhibition of injury-induced, smooth muscle cell proliferation. Other serotonin receptor blockers, such as pizotyline, cyproheptadine, methysergide, metergoline or mianserin give similar results. By adding reserpine to the regimen, a drug that depletes platelet serotonin stores (pretreatment for one week at 0.5 mg/kg i.p. q.d.), further reductions in smooth muscle cell proliferation are achieved. These results show that drugs which act to reduce the activity of serotonin within blood vessels prevent smooth muscle cell proliferation in the whole animal after vascular injury, and that such interventions prevent or reverse proliferative vascular lesions, which occur in atherosclerosis.

TABLE IV

Specific activity of aortic smooth muscle cell DNA after experimental vascular injury: Effects of Antiserotonin treatments

| | Specific Activity (CPM/ugDNA) |
|---|---|
| Control | 91.6 ± 13.7 (8) |
| Methiothepin-treated | 18.1 ± 5.3 (6) |
| Methiothepin plus reserpine-treated | 2.8 ± 1.3 (4) |

Experimental groups were significantly different from control (p / 0.01). Values shown are Mean ± Standard Error (N).

When the above test is repeated, the following specific activity (% of control) for smooth muscle cell DNA after vascular injury and antiserotonin treatment are found:

| | Specific Activity | Standard Error (%) | No. of Animals |
|---|---|---|---|
| Untreated | 100 | 15 | 7 |
| Vehicle treated | 92 | 21 | 5 |
| Reserpine | 68 | 12 | 4 |
| Methiothepin treated* | 23 | 4 | 10 |
| Methiothepin and Reserpine treated* | 10 | 3 | 8 |

*Statistically different from control (p / 0.01).

When the above procedure is carried out using various amounts of methiothepin, the following dose dependent specific activities are found:

| | Specific Activity | Standard Error (%) | No. of Animals |
|---|---|---|---|
| Vehicle | 100 | 16 | 7 |
| Methiothepin 0.3 mg/kg | 51 | 5 | 5 |
| Methiothepin 1.0 mg/kg | 24 | 4 | 6 |
| Methiothepin 3.0 mg/kg | 23 | 7 | 6 |
| Methiothepin 10.0 mg/kg | 20 | 7 | 6 |

EXAMPLE 5

This example demonstrates the reduction in the size of vascular lesions obtained with the serotonin receptor blocker, pizotyline.

Male Sprague-Dawley rats weighing 300–360 grams are individually ear tagged, housed and allowed to acclimate for two weeks prior to the start of the test. A constant formula rodent lab chow from Ralston Purina and water are available to the animals ad libitum.

For two days prior to de-endothelialization and for 14 days after, pizotyline at a dose of 25 milligrams per kilogram and placebo are administered by gavage in physiological saline to nine drug animals and 19 control animals. All animals are dosed between 8:00 and 10:00 A.M. daily. On the day of surgical de-endothelialization, the drug is administered intravenously (femoral vein) at 1/10 the oral dose in order to achieve optimal blood compound levels. There is a minimum period of five minutes between dose and actual insertion of the catheter. The animals are weighed daily at the time of dosing and behavior for each animal is recorded three to four hours after dosing. The animals are examined individually for approximately one minute for overt signs and symptoms and then returned to their cages.

On the day of de-endothelialization, the animals are anesthetized by ether inhalation and catheterization is carried out by the following procedure. The left femoral artery is exposed and lidocaine-HCl is applied locally to desensitize and dilate the blood vessel. The catheter balloon tip is advanced cephaled to the aortic arch region as determined through external catheter demarcations and inflated to a pre-established maximum diameter with approximately 900 mm Hg air pressure. The inflated catheter is drawn caudally to the bifurcation of the iliac arteries and deflated. This sequence is repeated three times as the catheter is twisted to assure symmetrical de-endothelialization of the vessel. The deflated balloon catheter is then removed and followed by ligation of the artery and area closure.

On the fourteenth day following de-endothelialization, whole body (beating heart) perfusion fixations are performed on the anesthesized and heparinized animals utilizing approximately 200 milliliters of a 3% buffered glutaraldehyde in 0.15 moles of sodium cacodylate at a pH of 7.4 under 90–100 mm hydrostatic pressure at 37° C. The entry site for the catheter is a left ventricular puncture and insertion is into the aortic arch. Efflux was collected via vacuum suction from the right atrium. The aorta is then removed and cut into 10 equal segments (#1–6 thoracic, #7–10 abdominal). The segments are subjected to an additional two-hour period in 3% buffered glutaraldehyde, buffer washing, and postfixation with 1% osmium tetroxide for 18 hours at 4° C.. Following the postfixation, the segments are infiltrated with Spurr's resin and cured at 70° C. Segments 2, 3, 8 and 9 are longitudinally sectioned at 0.5 micron thickness. A two-step polychromatic stain utilizing Stevenel's blue (2.0% $KMnO_4$, 1.3% methylene blue) and basic fuchsin (1.0%) is used to render histological differentiation to nuclear, cytoplasmic and extracellular (including neointimal) components. Lesions from the vessel segments are recorded as a sectional area in square microns ($\mu m^2$) utilizing a Zeiss standard microscope and the Videoplan computerized image analyzer; and the values are normalized to 1,000 $\mu m$ in length. Lesions exhibiting re-endothelialization are included in the analysis. Values from thoracic and abdominal segments are not pooled, as there is significant evidence to indicate a difference in rate of endothelial cell regrowth that affects lesion dimensions. The lesion-section area values are set out below in Table V:

TABLE V

Mean Lesion Area in Square Microns From Control and Treated Animals

| | Thoracic | Abdominal |
|---|---|---|
| Control | 50,283.1 | 60,310.3 |
| Pizotyline | 11,834.8 | 27,135.4 |

The animals treated with pizotyline consistently demonstrated reduced lesion formation in the thoracic segments with a mean reduction of 77% as compared to control lesion areas. Lesion formation in the abdominal segments are reduced by 55% in a similarly consistent manner.

Similar results are obtained with the following agents at the dose indicated:

| Agent | Dose (mg/kg) |
|---|---|
| Metergoline | 3.5 |
| Cyproheptadine | 25.0 |
| Methysergide | 46.0 |
| Spiroperidol | 4.6 |
| Ketanserin | 8.0 |
| Mianserin | 50.0 |
| Pipamperone | 20.0 |

EXAMPLES 5 AND 6

Tablets and Capsules Suitable for Oral Administration

Tablets and capsules containing the ingredients indicated below may be prepared by conventional techniques and are useful in preventing smooth muscle cell proliferation at a dose of one tablet or capsule a day.

| Ingredient | Weight (mg) Tablet | Weight (mg) Capsule |
|---|---|---|
| Pizotyline | 25 | 25 |
| Tragacanth | 10 | — |
| Lactose | 197.5 | — |
| Corn Starch | 25 | — |
| Talcum | 15 | — |
| Magnesium Stearate | 2.5 | — |

Similarly, tablets and capsules useful in preventing smooth muscle cell proliferation can be prepared using 10 milligrams of methiothepin and 0.5 milligrams of reserpine in place of the above pizotyline.

What is claimed is:

1. A method of inhibiting smooth muscle-cell proliferation in the blood vessel of an animal, which method comprises administering to the animal an effective serotonin-inhibiting amount of a serotonin-inhibiting agent which inhibits the action of platlet-released serotonin in the blood vessel.

2. The method of claim 1 which comprises administering the agent in an amount effective to reduce smooth muscle-cell proliferation by 20% to 100%.

3. The method of claim 1 which comprises administering the agent in an amount effective to reduce smooth muscle-cell proliferation by 40% to 95%.

4. The method of claim 1 which comprises administering the agent in a dose amount of 2 to 200 milligrams per kilograms of animal body weight.

5. The method of claim 1 which comprises administering the agent in a dose amount of 15 to 50 milligrams per kilograms of animal body weight.

6. The method of claim 1 which comprises administering the agent in a daily dose amount of from 1 to 1000 milligrams.

7. The method of claim 1 wherein the smooth muscle cell proliferation condition affecting the animal is atherosclerosis.

8. The method of claim 1 wherein the serotonin-inhibiting agent comprises a serotonin-receptor blocker agent which blocks the receptor sites for serotonin in the blood vessel.

9. The method of claim 8 wherein the serotonin-receptor blocker agent is selected from the group consisting of cyproheptadine, pizotyline, methiothepin, metergoline, methysergide, spiroperidol, ketanserin, mianserin, pipamperone and combinations thereof.

10. The method of claim 1 wherein the serotonin-inhibiting agent comprises a serotonin-storage blocker agent which inhibits the storage of serotonin by platelets in the blood vessel.

11. The method of claim 10 wherein the serotonin-storage blocker agent comprises reserpine.

12. The method of claim 1 wherein the serotonin-inhibiting agent comprises a combination of a serotonin-receptor blocker agent and a serotonin-storage blocker agent.

13. The method of claim 12 wherein the serotonin-storage blocker agent comprises reserpine.

14. The method of claim 1 wherein the serotonin-inhibiting agent comprises a serotonin-uptake blocker agent which inhibits the uptake of serotonin by platelets in the blood vessel.

15. The method of claim 14 wherein the serotonin-uptake blocker agent comprises fluoxetine or amitriptyline.

16. The method of claim 14 wherein the serotonin-inhibiting agent comprises a tryptophan-hydroxylase-inhibiting agent which inhibits the conversion of tryptophan to serotonin in the blood vessel.

17. The method of claim 16 wherein the tryptophan-hydroxylase-inhibiting agent comprises p-chlorophenylalanine.

18. The method of claim 1 wherein the serotonin-inhibiting agent comprises a 5-hydroxytryptophan-decarboxylase-inhibiting agent which inhibits the conversion of tryptophan to serotonin in the blood vessel.

19. The method of claim 18 wherein the 5-hydroxytryptophan-decarboxylase-inhibiting agent comprises carbidopa.

20. The method of claim 1 wherein the serotonin-inhibiting agent comprises a blood platelet inhibition agent which acts as an inhibitor of platelet activity to decrease serotonin release in the blood vessel.

21. The method of claim 1 which comprises administering in combination a serotonin-receptor blocker agent and a platelet-inhibiting agent, to decrease platelet aggregation and adhesion in the blood vessel.

22. The method of claim 21 wherein the platelet-inhibiting agent acts to raise platelet cyclic AMP, acts to decrease platelet thromboxane $A_2$, or acts to block calcium influx into platelets.

23. The method of claim 22 wherein the blood platelet inhibiting agent comprises verapamil as a calcium channel blocker.

24. The method of claim 1 which comprises administering a combination of at least two different serotonin-inhibiting agents selected from the group of agents consisting of a tryptophan hydroxylase inhibitor, a peripheral decarboxylase inhibitor, a serotonin-uptake blocker, a serotonin-storage blocker, an antiplatelet drug, and a serotonin-receptor blocker.

25. The method of claim 1 wherein the serotonin-inhibiting agent comprises a diet lean in tryptophan.

26. A method of inhibiting an atherosclerotic condition caused by smooth muscle-cell proliferation in the blood vessel of an animal, which method comprises administering to the animal an effective serotonin-inhibiting dose amount of 2 to 200 milligrams per kilograms of animal body weight of a serotonin-inhibiting agent which inhibits the action of platelet-released serotonin in the blood vessel to reduce smooth muscle-cell proliferation by 20% to 100%, and which agent comprises in combination a serotonin-receptor blocker agent selected from the group consisting of cyproheptadine, pizotyline, methiothepin, metergolin, methysergide, spiroperidol, ketanserin, mianserin, pipamperone and combinations thereof, and a serotonin-storage blocker agent which comprises reserpine.

27. A pharmaceutical composition for use in inhibiting smooth muscle-cell proliferation in a blood vessel of an animal, which composition comprises a serotonin-inhibiting amount of at least two serotonin-inhibiting agents which inhibit the action of platelet-released serotonin in the blood vessel, the agents selected from the group consisting of:
(a) a serotonin-receptor blocker agent which blocks the receptor sites for serotonin in the blood vessel;
(b) a serotonin-storage blocker agent which inhibits the storage of serotonin by platelets in the blood vessel;
(c) a serotonin-uptake blocker agent which inhibits the uptake of serotonin by platelets in the blood vessel; and
(d) a platelet-inhibiting agent which decreases platelet aggregation or platelet adhesion in the blood vessel.

28. The composition of claim 27 wherein the serotonin-receptor blocker agent is selected from the group consisting of cyproheptadine, pizotyline, methiothepin, metergoline, methysergide, spiroperidol, ketanserin, mianserin, pipamperone and combinations thereof.

29. The composition of claim 27 wherein the serotonin-storage blocker agent comprises reserpine.

30. The composition of claim 27 wherein the serotonin-uptake blocker agent comprises fluoxetine or amitriptyline.

31. A pharmaceutical composition for use in inhibiting smooth muscle-cell proliferation in a blood vessel of an animal, which composition comprises a combination of the two serotonin-inhibiting agents in a serotonin-inhibiting amount, which agents inhibit the action of platelet-released serotonin in the blood vessel and which agents comprise:
(a) a serotonin-receptor blocker agent selected from the group consisting of cyproheptadine, pizotyline, methiothepin, metergolin, methysergide, spiroperidol, ketanserin, mianserin, pipamperone and combinations thereof and which blocks the receptor sites for serotonin on smooth muscle cells in the blood vessel; and
(b) a serotonin-storage blocker agent which inhibits the storage of serotonin by platelets in the blood vessel and which comprises reserpine.

* * * * *